United States Patent [19]

Ruhle

[11] 4,266,186
[45] May 5, 1981

[54] METHOD OF TESTING SILICON CONTENT IN ALUMINIUM ALLOYS

[75] Inventor: Martin Ruhle, Stuttgart, Fed. Rep. of Germany

[73] Assignee: Mahle GmbH, Stuttgart, Fed. Rep. of Germany

[21] Appl. No.: 15,134

[22] Filed: Feb. 26, 1979

[30] Foreign Application Priority Data

Mar. 2, 1978 [DE] Fed. Rep. of Germany ....... 2808902

[51] Int. Cl.³ ............................................ G01R 27/02
[52] U.S. Cl. .................................. 324/65 R; 324/62; 324/64; 324/158 P
[58] Field of Search ............... 324/65 R, 64, 62, 65 P, 324/158 P

[56] References Cited

U.S. PATENT DOCUMENTS

| | | | |
|---|---|---|---|
| 1,718,687 | 6/1929 | Enlund | 324/64 |
| 1,893,700 | 1/1933 | Enlund | 324/64 |
| 2,124,578 | 7/1938 | Knerr et al. | 324/64 |
| 2,854,626 | 9/1958 | Davidson et al. | 324/64 |
| 3,207,981 | 9/1965 | Marsh et al. | 324/64 X |
| 3,416,078 | 12/1968 | Boncuk et al. | 324/64 |
| 3,735,254 | 5/1973 | Severin | 324/158 P |
| 3,916,304 | 10/1975 | Roemer et al. | 324/65 R X |
| 3,995,213 | 11/1976 | Robinson et al. | 324/64 |

FOREIGN PATENT DOCUMENTS

| | | | |
|---|---|---|---|
| 85511 | 2/1936 | Sweden | 324/64 |
| 1030848 | 5/1966 | United Kingdom | 324/64 |

*Primary Examiner*—Stanley T. Krawczewicz
*Attorney, Agent, or Firm*—Murray and Whisenhunt

[57] ABSTRACT

The invention provides a method of testing silicon distribution in aluminium-silicon alloys by drawing a conductor across the surface of the alloy and measuring the changes of electric resistance between the conductor and the alloy.

5 Claims, 1 Drawing Figure

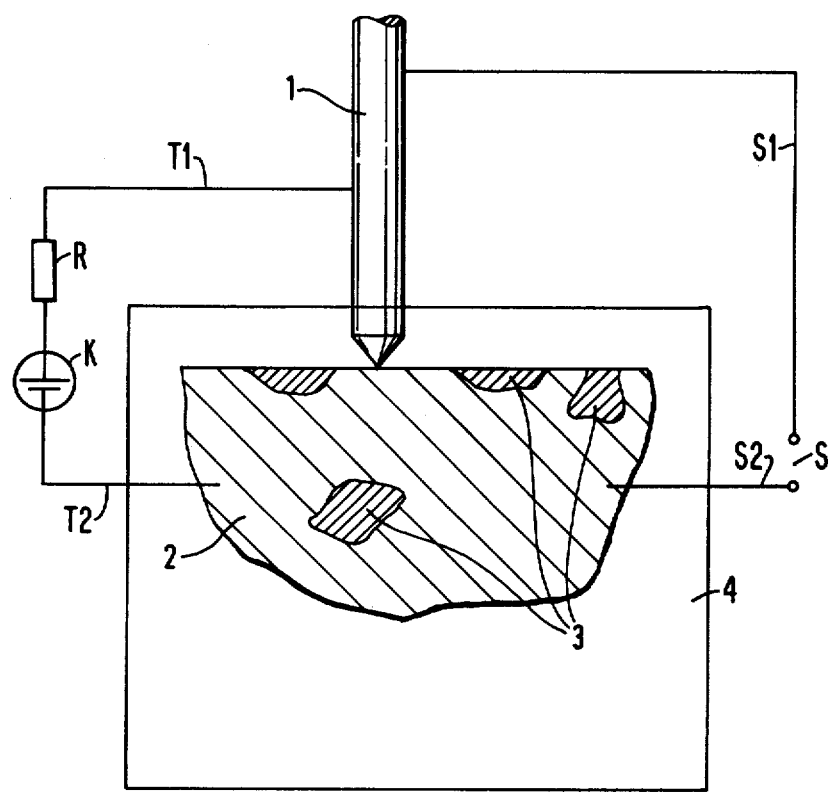

METHOD OF TESTING SILICON CONTENT IN ALUMINIUM ALLOYS

BACKGROUND OF THE INVENTION

The assessment of primary silicon constituents on the surface of silicon-containing aluminium alloys is as a rule effected light-optically with a microscope. However, a requirement for such a test is that the surface to be tested is as smooth as a mirror so as to bring about the required good reflection of light. Such a surface is in practice obtained by grinding and polishing the workpiece surface to be looked at. A microscopic evaluation is thus only possible if either the required dead-smooth surface is given from the outset or such a surface is specially produced for the performance of the test.

There are cases where the test is to be effected on the surface of a finished workpiece and where the surface of this workpiece is neither fine-polished nor allowed to be fine-polished. An example are the cylinder bores of internal-combustion-engine blocks consisting of a silicon-containing aluminium alloy. For the attainment of a good running or sliding behaviour between the piston and the cylinder wall, the cylinder surfaces are honed in a very specific manner. If one wants to test the primary silicon distribution over, for example, the entire height of the cylinder bore on such a surface, which must not be charged for test purposes, a microscopic inspection is ruled out because without receiving additional treatment the surface is unsuitable for such an inspection. A non-destructive test is thus not possible with the use of a microscope.

Another possibility of testing the distribution of primary silicon crystals on the surface of an aluminium alloy is the so-called imprinting method. In this method, foils are pressed on the surface to be tested and the impressions in the foil are subsequently evaluated. However, this method only works if the silicon particles project from the surface to be tested, i.e. if differences in height exist between the silicon to be determined and the surrounding aluminium matrix. If this is not the case, such an imprinting method by means of a foil fails.

Another method for the detection of silicon in the surface is the measurement of the surface roughness. But this method also necessitates a projection of the silicon particles from the remaining aluminium matrix.

In summary, it can be said that the hitherto known measuring methods allow a non-destructive test only in exceptional cases, namely when the surface formations required for the various measuring methods happen to be provided.

OBJECT OF THE INVENTION

To remedy this situation and to provide a method allowing a reliable statement to be obtained about the distribution of primary silicon on the surface of silicon-containing aluminium alloys, irrespective of the surface finish that happens to be present, is the object of the present invention.

SUMMARY OF THE INVENTION

According to the invention I provide a method for the non-destructive testing of the primary silicon distribution on the surface of silicon-containing aluminium alloys comprising searching the surface of the alloy step by step with the point of a pin made of a conductive material, the pin and the alloy being connected to an electric voltage source, and measuring the change of the electric contact resistance between the point of the pin and the surface of the alloy thereby providing a measurement for the distribution of the primary solution on the surface.

Other subsidiary features of the invention will be described with reference to the accompanying drawing.

BRIEF DESCRIPTION OF DRAWING

The method is diagrammatically shown in the drawing.

The principle of the measurement is as follows:

A hard metallic point of a measuring pin 1 is guided under minimal pressure across the surface of the hypereutectic Al—Si alloy sample 2 to be examined. The terminals are connected to a distance-time recorder (not shown) which includes a source of electrical current. The pin is connected by conductor T1 to a resistance R which is connected in series with a constant voltage device K and this in turn is connected by conductor T2 to the workpiece 2. The electric contact resistance between the point of the measuring pin 1 and the sample 2 is measured by the recorder. When the point of the measuring pin 1 encounters a primary silicon particle 3, there occurs a marked increase in the resistance. This is caused both by the fact that the surface on which the hard point rests on the hard silicon is smaller than the solt Al matrix and by the poor electric conductivity of the silicon as a semi-metal.

An example of a measurement will be given hereinafter. The measuring pin 1 with a hard-metal point having a point angle of 90° is guided across a grease-free honed surface of a hypereutectic Al-Si alloy (sample 2) under a bearing load of 4 p.

The point of the measuring pin 1 and the sample 2 are connected to a voltage source of 500 mV at a source impedance of 500 Ohm. The voltage drop between the point of the measuring pin 1 and the sample 2 is measured and is recorded on the distance-time recorder, namely a potentiometer-type instrument or a light-beam instrument, depending on the probing speed. The current flowing through the measuring point is approximately 1 mA. The measurement is carried out under a suitable ambient fluid 4 e.g. alcohol, so as to avoid the test point being burnt off, for current densities of the order of as much as 10 $A/nm^2$ arise due to the small contact surface. The feed of the measuring point is effected by a hydraulically damped pneumatic cylinder.

The measuring pin points show a high degree of wear when hardened steel is used and can only be used for one measurement. However, if hard metal is used, the point does not show any traced of wear even after several measurements have been effected.

Although a point angle of 90° for the point of the measuring pin has been well proven in trails, it is presumably not the optimum. The optimum will be probably at angles of less than 90°, with the load resting on the measuring pin having to be reduced. Load and angle have to be optimally co-ordinated.

The test signals obtained by searching can be processed both by analogue and digital means or in a combination thereof. The description of the structural constitution can be made through the detection of the following parameters:

The number of particles or the point of intersection frequency per unit distance (e.g. 10 mm) as they are distributed over the cylinder height. The square of the points of intersection per unit length, divided by the mean Si size, gives a measurement for the number of particles per unit area.

The area proportion of the primary Si or the sum of all the pulse lengths during the searching of a unit distance (e.g. 1 cm) gives the primary Si quantity and allows the determination of its distribution over the cylinder height.

The mean Si size or the quotient from the sum of all the pulse lengths by the number of the points of intersection in its distribution over the cylinder height.

The size category distribution of the Si

The test pulse are added up in different stores according to their length and a Gaussian normal distribution is made for different cylinder areas.

Primary Si segregations

Si particles which are closely adjacent to one another are measured as one particle by the electronic extension of the test pulses. A comparison of the Si number or the mean size with the unmanipulated values gives a measure for the degree of the primary Si segregations.

The acquisition of the measured values can be effected through a tape recording (stereo recorder). Such a recording is suitable for evaluation on a calculator. It is important for application in practice that in cases of doubt a retrospective inspection on the screen in possible. Furthermore, a rough preliminary check would also be possible acoustically.

I claim:

1. A method for the non-destructive testing of silicon-containing aluminium alloys containing discrete primary silicon inclusions comprising moving the tip of a pin of conductive material along the surface of the alloy so as alternately to contact silicon inclusions and aluminium, connecting the pin and alloy in an electrical circuit, measuring change of electrical units and thereby ascertaining the size and distribution of the individual silicon inclusions.

2. A method as claimed in claim 1 wherein the voltage drop between the tip of the pin and the alloy is measured and is recorded on a distance-time recorder.

3. A method according to claim 1, wherein the point of the pin has a point angle which is less than or equal to 90°.

4. A method according to claim 1, wherein hard metal is used as the material for the point of the measuring pin.

5. A method according to claim 1 wherein the pin point is surrounded by an ambient fluid protective against burning.

* * * * *